United States Patent [19]

Sato et al.

[11] Patent Number: 4,612,190

[45] Date of Patent: Sep. 16, 1986

[54] GROWTH INHIBITOR FOR CARIOGENIC BACTERIA

[75] Inventors: Toshiya Sato; Kenichi Asano; Yuzo Yamaguchi, all of Kanagawa, Japan

[73] Assignee: Takasago Perfumery Co., Ltd., Tokyo, Japan

[21] Appl. No.: 671,838

[22] Filed: Nov. 15, 1984

[30] Foreign Application Priority Data

Nov. 15, 1983 [JP] Japan ................................ 58-213336

[51] Int. Cl.$^4$ ...................... A61K 7/16; A61K 31/075
[52] U.S. Cl. ...................................... 424/49; 514/721; 514/835
[58] Field of Search ...................... 514/720, 721, 835; 424/49

[56] References Cited

PUBLICATIONS

J. Pharm. Sci. 63(12), Dec. 1974, pp. 1905–1907.

*Primary Examiner*—Douglas W. Robinson
*Attorney, Agent, or Firm*—Sughrue, Mion, Zinn, Macpeak & Seas

[57] ABSTRACT

A growth inhibitor for cariogenic bacteria which comprises containing therein dihydroguaiaretic acid as an active ingredient. In particular, the effect of growth inhibition to *Streptococcus mutans* RIMD 3125001 strain can be obtained at a concentration of 1/50,000.

13 Claims, No Drawings

GROWTH INHIBITOR FOR CARIOGENIC BACTERIA

FIELD OF THE INVENTION

The present invention relates to a growth inhibitor for cariogenic bacteria. More particularly, it relates to a growth inhibitor for cariogenic bacteria which comprises containing therein dihydroguaiaretic acid as an active ingredient.

BACKGROUND OF THE INVENTION

The caries is generally referred to as a decayed tooth. It is caused by *Streptococcus mutans* and other lactic acid bacteria indigenous to the oral cavity which form lactic acid in the bacterial plaque resulting from sucrose etc., in the food. The lactic acid dissolves calcium in the tooth. (This is called decalcification.)

Heretofore, several attempts have been made to prevent caries. They include use of antibiotics, fungicides, an enzyme which dissolves cell walls and medicines having the antibacterial action to prevent the growth of cariogenic bacteria. They also include use of polysaccharide hydrolase to prevent the formation of bacterial plaque. However, those have a disadvantage of disturbing the bacterial flora in the oral cavity and intestine and destroying the natural balance among bacteria. In addition, the use of antibiotics tend to produce side effects. These disadvantages in practical use have not been overcome yet.

In view of these circumstances, as a result of a series of investigations in search for a material having a high antibacterial activity specifically for cariogenic bacteria, it has been found that some of natural vegetable oleoresin have such antibacterial activity.

As a result of further investigations on the vegetable oleoresin (extract by organic solvents) which is effective to inhibit the growth of cariogenic bacteria, it has been found that dihydroguaiaretic acid which is one component therein has the properties to well achieve the object of this invention. The present invention has been attained on the basis of this finding.

SUMMARY OF THE INVENTION

Accordingly, an object of this invention is to provide a growth inhibitor for cariogenic bacteria which comprises containing therein dihydroguaiaretic acid as an active ingredient.

DETAILED DESCRIPTION OF THE INVENTION

The dihydroguaiaretic acid used in this invention is the conventional compound represented by the structural formula:

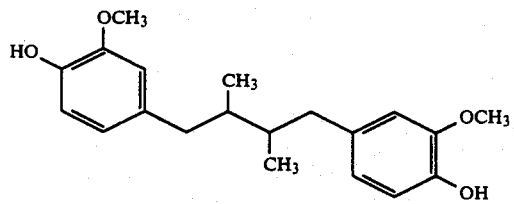

This compound is a colorless crystal having a melting point of 87° to 88° C.

The dihydroguaiaretic acid is contained in, for example, *Machilus edulis* K., *Guaiacum officinale* L. and *Schizandra chinensis* B. Banda Mace and Siaum Mace which are used in general spices for food and Penang Mace which is used in preparation of essential oils and/or oleoresin have the name: *Myristica frangrans* H. It is not yet reported that dihydroquaiaretic acid is present in the mace of such a species.

On the other hand, according to the inventors' experiments, it has been found that Pupua Mace (name: *Myristica argentea*) having a bad odor and in which the yield of essential oil is poor contains dihydroguaiaretic acid. Therefore, the Pupua Mace can be used as the starting material for dihydroguaiaretic acid.

Dihydroguaiaretic acid can be isolated from these oleoresins by the conventional method such as solvent extraction or silica gel column chromatography.

The cariogenic bacteria growth inhibitor containing dihydroguaiaretic acid according to this invention can be used in the form of a solution by dissolving it in an organic solvent such as ethanol, propylene glycol or glycerin, which causes no problem in the oral cavity, because dihydroguaiaretic acid is hardly soluble in water but soluble in an organic solvent such as alcohols. The inhibitor can also be used in the form of an emulsion by emulsifying it in water using a surfactant such as Span 20 (a product of Atlas Powder Co.). Moreover, it is also possible to make such an emulsion into a water-dispersible powder by adding dextrin thereto followed by spray drying. Thus, the growth inhibitor of this invention can be used in various forms depending upon the purpose of use thereof. The inhibitor can, of course, be used in combination with other medicines, if desired.

Dihydroguaiaretic acid performs bacteriostatic action on cariogenic bacteria, and its bactericidal action is mild. Therefore, dihydroguaiaretic acid can be suitably added to chewing gum, candy, troche, wheat gluten, and other foods which stay in the oral cavity for a long time, in the form of a propylene glycol or glycerin solution. Further, dihydroguaiaretic acid can be suitably added to toothpaste and mouth wash in the form of an emulsion and to tooth powder in the form of a powder.

The growth inhibitor of this invention can completely inhibit the growth of *Streptococcus mutans* RIMD 3125001 strain which causes caries under the anaerobic condition in the medium, at a concentration of 1/50,000 of dihydroguaiaretic acid. On the other hand, the growth inhibitor of the invention was used at the same concentration to intestinal bacteria such as *Bacteroides microfusus* IPCR 1009 strain and *Escherichia coli* ATCC 10789 strain which are aerobe, and *Bifidobacterium adolescents* ATCC 15705 strain which is obligate anaerobe; and general microorganisms such as *Pseudomonas aeruginosa, Bacillus subtilis, Staphylococcus aureus, Aspergillus nigar, Candida albicans* and *Klebsiella pneumoniae*. As a result, the growth inhibitor did not exhibit at all the growth inhibiting effect against the intestinal bacteria. Further, the growth inhibitor exhibited a slight antibacterial action against gram-positive bacteria such as *Staphylococcus aureus* or *Bacillus subtilis* under the aerobic conditions, but did not substantially exhibit any effect against the gram-negative bacteria and molds.

The effectiveness of the growth inhibitor of this invention was not affected by a surfactant such as sodium laurylsulfonate or "Span 20" (ATLAS POWDER CO.).

Where the cariogenic bacteria growth inhibitor of this invention is incorporated into foods or dentifrice, it is preferred that the concentration thereof be slightly higher than the effective concentration (1/50,000), because the contact time of the food or dentifrice to cariogenic bacteria is comparatively short.

Oleoresin containing dihydroguaiaretic acid may be used for the object of this invention. It is, however, preferred that the oleoresin be purified completely or to a certain extent so as not to give off an unpleasant odor in the oral cavity due to other components.

The cariogenic bacteria growth inhibitor of this invention is specifically effective to *Streptococcus mutans* and its effect of inhibiting the growth of bacteria is not affected by a surfactant. Dihydroguaiaretic acid is highly safe because it is a component contained in the oleoresin which is natural food. In addition, it tastes only a little and gives no unpleasant feeling when put in the mouth.

This invention is now described in more detail by reference to the following Production Examples and Examples but is not limited thereto. Unless otherwise indicated, all percents, parts, ratios and the like are by weight.

PRODUCTION EXAMPLE 1

100 g of Pupua Mace powder was dipped in 500 ml of 95% ethanol to extract for 2 days at room temperature. The extract was concentrated to obtain 9 g of a reddish brown oil. The oil was subjected to a column chromatography (silica gel 450 g) with a mixed solvent of n-hexane and ethyl ether (2:1 by volume) and the resulting eluate was concentrated to obtain 0.9 g of colorless prism-like crystals.

It was confirmed from the comparison between the following physical found values and the values mentioned in literature that the crystals were dihydroguaiaretic acid.

m.p. 87°-88° C., $[\alpha]_D^{25} \pm 0°$

IR (cm$^{-1}$) 3,470, 1,820, 1,600

NMR (CCl$_4$) ($\delta$): 0.84 (6H, $\delta$, J=6.8 Hz), 1.5-2.0 (2H, m), 2.30 (2H, d×d, J=8.3, 14.4 Hz), 2.75 (2H, d×d, J=4.7, 14.4 Hz), 3.85 (6H, s), 5.48 (2H, s), 6.6-6.95 (6H, m)

PRODUCTION EXAMPLE 2

4.6 kg of *Schizandra chinensis* B. was added to 23 l of petroleum ether to extract over day and night while sometimes stirring at room temperature. 550 g (yield 12%) of a blackish brown oily product was obtained. The product was subjected to a silica gel column chromatography with a mixed solvent of benzene and acetone (1:1 by volume) and the resulting eluate was concentrated to obtain 11 g of a pale yellowish brown oil component.

The oily component was further subjected to a column chromatography (silica gel 240 g) with a mixed solvent of ethyl acetate and n-hexane (4:1 by volume) and the solvent in the resulting eluate was evaporated to obtain 520 mg of a substantially colorless oil component.

This oil component was recrystallized with a mixed solvent iof n-hexane and acetone (7:3 by volume) to obtain 102 mg of prism-like crystals.

EXAMPLE 1

2.0 g of dihydroguaiaretic acid was dissolved in 98 g of official ethyl alcohol with stirring at room temperature to give 100 g of a solution.

This solution was added to the heart infusion agar medium. *Streptococcus mutans* RIMD 3125001 (designated as A in Table) was transplanted by stabbing to this medium. Incubation was conducted at 37° C. for 72 hours. No growth was observed in the medium containing the solution at a concentration of 1/1,000 (i.e., 1/50,000 calculated as dihydroguaiaretic acid). Growth was barely observed in the medium containing the solution at a concentration of 1/1,600 (i.e., 1/80,000 calculated as dihydroguaiaretic acid).

Then, *Bacteroides microfusus* IPCR 1009 (designated as B in Table) and *Escherichia coli* ATCC 10789 (designated as C in Table) were transplanted to the above-mentioned medium. Incubation was conducted under the aerobic condition at 37° C. for 72 hours. Their growth was inhibited at a concentration of 1/2,000 as dihydroguaiaretic acid.

*Bifidobacterium adolescentis* ATCC 15705 (designated as D in Table) was transplanted to the same medium as mentioned above, and incubation was conducted under the anaerobic condition at 37° C. for 72 hours. The growth was inhibited at a concentration of 1/7,500 as dihydroguaiaretic acid.

The same test as above was conducted under the aerobic condition for *Pseudomonas aeruginosa* (E), *Bacillus subtilis* (F), *Staphylococcus aureus* (G), *Aspergillus nigar* (H), *Candida albicans* (I), and *Klebsiella pneumoniae* (J). The results obtained are shown in Table below.

TABLE

| Designation of Bacteria | Concentration for Growth Inhibition (as dihydroguaiaretic acid) |
|---|---|
| A | 1/50,000 |
| B | 1/2,000 |
| C | 1/2,000 |
| D | 1/7,500 |
| E | 1/500 |
| F | 1/5,000 |
| G | 1/5,000 |
| H | 1/1,000 |
| I | 1/2,000 |
| J | 1/1,000 |

EXAMPLE 2

2.0 g of dihydroguaiaretic acid was dissolved in 6 ml of official ethyl alcohol, and glycerin was then added thereto to give 100 g of a solution.

This solution was added to two kinds of heart infusion agar media, one containing 1.0 g of sodium laurylsulfonate and the other, 1.0% of "Span 20". *Streptococcus mutans* RIMD 3125001 was transplanted to the media. Incubation was conducted at 37° C. for 72 hours. The concentration for growth inhibition was 1/1,000 (i.e., 1/50,000 calculated as dihydroguaiaretic acid) in both cases. This indicates that the effectiveness of the growth inhibitor is not affected by the surfactant used.

EXAMPLE 3

| | parts by weight |
|---|---|
| Calcium hydrogenphosphate, dibasic | 50 |
| Sodium carboxymethyl cellulose | 1 |
| Sodium lauryl sulfate | 1.5 |
| Glycerin | 25 |
| Saccharin | 0.2 |
| Glycerin containing 1 wt % of dihydroguaiaretic acid | 1 |
| Mint type flavor | 1 |
| Water | 20.3 |
| | 100 |

The above components were sufficiently kneaded to prepare a tooth paste.

EXAMPLE 4

| | parts by weight |
|---|---|
| 90% Ethanol | 20 |
| Saccharin | 0.2 |
| Sodium N—acyl methyl taurate | 0.5 |
| Gelatin | 0.5 |
| 90% Ethanol containing 1 wt % of dihydroguaiaretic acid | 1.0 |
| Mint type flavor | 0.5 |
| Water | 77.3 |
| | 100 |

The above components were mixed to prepare a mouth wash.

EXAMPLE 5

| | parts by weight |
|---|---|
| Gum base | 22 |
| Calcium carbonate | 2 |
| Saccharin | 0.1 |
| Sorbitol | 14 |
| Lactose | 60 |
| Glycerin containing 1 wt % of dihydroguaiaretic acid | 1 |
| Mint type flavor | 0.9 |
| | 100 |

The above components were well kneaded at 0° C., and after cooling, the blend was rolled and cut to prepare a chewing gum.

EXAMPLE 6

| | parts by weight |
|---|---|
| Gum arabic | 6 |
| Glucose | 72 |
| Lactose | 17 |
| Potassium phosphate, dibasic | 0.2 |
| Potassium phosphate, monobasic | 0.1 |
| Glycerin containing 1 wt % of dihydroguaiaretic acid | 1 |
| Mint type flavor | 0.7 |
| Magnesium stearate | Proper amount |

The above components except magnesium stearate were sufficiently kneaded to prepare a plastic mass. The plastic mass was rolled and dried. After magnesium stearate was added, the mixture was cut to prepare a troche.

While the invention has been described in detail and with reference to specific embodiments thereof, it will be apparent to one skilled in the art that various changes and modifications can be made therein without departing from the spirit and scope thereof.

What is claimed is:

1. A process for inhibiting the growth of cariogenic bacteria locally in the mouth which comprises administering locally to the mouth an amount of dihydroguaiaretic acid effective to inhibit growth of *Streptococcus mutans*, admixed with an acceptable carrier.

2. The process of claim 1 wherein said *Streptococcus mutans* is *Streptococcus mutans* RIMD 3125001.

3. The process of claim 1 wherein said dihydroguaiaretic acid is administered using a composition containing a concentration of dihydroguaiaretic acid of 1/50,000 or higher.

4. The process of claim 3 wherein the dihydroguaiaretic acid is administered in admixture with food.

5. The process of claim 3 wherein the dihydroguaiaretic acid is administered in admixture with a dentifrice.

6. The process of claim 3 wherein the dihydroguaiaretic acid is administered in admixture with a mouth wash.

7. The process of claim 3 wherein the dihydroguaiaretic acid is administered in admixture with a troche.

8. A composition for inhibiting growth of cariogenic bacteria in the mouth, which composition comprises, as an active ingredient an amount of dihydroguaiaretic acid effective to inhibit growth of *Streptococcus mutans* when administered locally to the mouth, admixed with a food.

9. A dentifrice for inhibiting growth of cariogenic bacteria in the mouth, which dentifrice comprises, as an active ingredient an amount of dihydroguaiaretic acid effective to inhibit growth of *Streptococcus mutans* when administered locally to the mouth, admixed with a tooth powder or a tooth paste.

10. A mouth wash composition for inhibiting growth of cariogenic bacteria in the mouth, which composition comprises, as an active ingredient an amount of dihydroguaiaretic acid effective to inhibit growth of *Streptococcus mutans* when administered locally to the mouth, admixed with a mouth wash.

11. A chewing gum for inhibiting growth of cariogenic bacteria in the mouth, which chewing gum comprises, as an active ingredient an amount of dihydroguaiaretic acid effective to inhibit growth of *Streptococcus mutans* when administered locally to the mouth, admixed with a chewing gum.

12. The composition of claim 8 wherein said food is a candy.

13. A troche for inhibiting growth of cariogenic bacteria in the mouth, which troche comprises as an active ingredient an amount of dihydroguaiaretic acid effective to inhibit growth of *Streptococcus mutans* when administered locally to the mouth, admixed with a troche composition.

* * * * *